United States Patent [19]
Falorni et al.

[11] Patent Number: 6,093,396
[45] Date of Patent: Jul. 25, 2000

[54] MODIFIED GLUTAMIC ACID DECARBOXYLASE (GAD)

[75] Inventors: Alberto Falorni, Perugia, Italy; Ake Lernmark, Seattle, Wash.; John Robertson, Nacka; Anders Essen-Moller, Stockholm, both of Sweden

[73] Assignee: Diamyd Therapeutics AB, Stockholm, Sweden

[21] Appl. No.: 09/043,930

[22] PCT Filed: Sep. 27, 1996

[86] PCT No.: PCT/SE96/01210

§ 371 Date: Jun. 23, 1998

§ 102(e) Date: Jun. 23, 1998

[87] PCT Pub. No.: WO97/12034

PCT Pub. Date: Apr. 3, 1997

[51] Int. Cl.[7] ............................... A61K 38/46; C12N 9/18; C12N 15/00; C12N 1/20; C07H 21/04
[52] U.S. Cl. ...................... 424/94.6; 435/197; 435/320.1; 435/252.3; 435/254.2; 435/348; 435/325; 536/232

[58] Field of Search .................. 424/94.1, 94.6; 536/23.2; 435/320.1, 252.3, 354.2, 348, 419, 197

[56] References Cited

FOREIGN PATENT DOCUMENTS

WO 92/05446  4/1992  WIPO .
WO 92/20811  11/1992  WIPO .
WO 95/27051  10/1995  WIPO .

*Primary Examiner*—Karen Cochrane Carlson
*Assistant Examiner*—Devesh Srivastava
*Attorney, Agent, or Firm*—Young & Thompson

[57] ABSTRACT

A modified GAD especially characterized by a substantially preserved immunogenicity in connection with diabetes compared with a non-modified GAD and a reduced or non-existent effectivity in connection with a GABA-synthesis. The invention relates also to a method for manufacturing a modified GAD, a method for supplying a modified GAD, nucleotide sequence encoding the modified GAD, a vector containing the nucleic acid sequence, a host, a pharmaceutical composition comprising modified GAD and use thereof for treating and/or preventing autoimmune disorders such as IDDM.

11 Claims, No Drawings

MODIFIED GLUTAMIC ACID DECARBOXYLASE (GAD)

The present invention relates to a genetically-modified recombinant form of the 65 kDa human glutamic acid decarboxylase (hGAD65) that retains structural integrity for immuno-reactivity characteristic of the unmodified form, but that is without (or with considerably reduced) enzyme activity. The novel modified GAD is advantageously used in pharmaceutical compositions for treating autoimmune diseases.

BACKGROUND OF THE INVENTION

The inhibitory neurotransmitter γ-aminobutyric acid (GABA), derived from L-glutamic acid by GAD is present in brain as well as several tissues outside the central nervous system. Biological functions of GAD and GABA extend beyond regulation of neurotransmission to include effects on the immune system as well as modulation of cell proliferation, protein synthesis and metabolism.

GAD has recently been associated with autoimmune insulin-dependent diabetes mellitus (IDDM) (Boekkeskov et al, Nature 347:151 (1990), incorporated by reference) because of the increased incidence of IDDM in patients with stiff-man syndrome, a disease associated with autoantibodies against GAD. Antibodies from diabetic sera have also been shown to bind GAD. At least two different GAD, i.e. GAD 65 and 67 have been identified and sequenced in human beings. hGAD65 and hGAD67 have several epitopes in common. However, different epitopes are involved in different reactions and contexts.

Binding of the coenzyme pyridoxal-5'-phospate (PLP) to GAD was first reported by Roberts & Frankel in 1951 (J. Biol. Chem. 188:789, fully incorporated in the description by reference), and formation of a Schiff base during GAD-mediated decarboxylation was subsequently proposed by W T Jenkins 1961, Fed. Proc. 20:978 (fully incorporated in the description by reference) (i.e. referenced in Roberts & Simonsen 1963, Biochem. Pharmacol. 12:113–134, fully incorporated in the description by reference). Accordingly, PLP has been identified as a critical co-factor in decarboxylation by GAD.

Cloning of GAD is disclosed in WO92/05446 and WO92/20811 (both incorporated by reference).

Location of the PLP binding site within the amino acid sequence of hGAD65 was enabled by publication of the cDNA sequence of this enzyme (P.N.A.S. 88:8337, fully incorporated in the description by reference). The site was found because of the homology centred around the amino acid lysine at a/a #396 in hGAD65—to the sequence: X-His-Lys-X that was previously published as the PLP binding site in crystallised *E.coli* GAD (Biochemistry 9:226–233; Biochemistry 13:670–676, both of which are fully incorporated in the description by reference).

This region in hGAD65 has the following amino acid sequence (SEQ ID NOS:9 and 10):

| Thr | Trp | Asn | Pro | His | Lys* | Met | Met | Gly | Val |
|-----|-----|-----|-----|-----|------|-----|-----|-----|-----|
| T | W | N | P | H | K* | M | M | G | V |
| • | | | | | • | | | | • |
| #391 | | | | | #396 | | | | #400 |

*selected herein for mutation to change K to Arg (R)

This homology in this region has subsequently been confirmed by Lernmark (unpublished) using computer homology matches to ca. 10 other PLP-binding (non-GAD) proteins.

The approach of the present invention is a novel GAD without enzyme activity by mutating a single codon in the PLP binding site in the cDNA sequence for hGAD65. This results in the substitution of a single amino acid that is incapable of supporting wild-type enzyme activity.

As the lysine at #396 has been identified as critical for enzyme activity (via formation of a Schiff base during GAD-mediated decarboxylation), the present invention is directed to substitute an amino acid incapable of Schiff base formation at position #396 as a subtle means of achieving this effect.

In addition, a "conservative amino acid substitution" (i.e. replacement of lysine by an amino acid of comparable size and hydrophobicity) is intended to minimise any structural or conformational changes to the hGAD65 protein, and thereby avoid alterations to either antigenic etitopes or T cell determinants originally present in recombinant human GAD (rhGAD65).

SUMMARY OF THE INVENTION

The present invention relates to a modified, non-enzymically active hGAD65 retaining the immunoreactive characteristics of wild type hGAD65, wherein amino acid #396 has been altered an L-amino acid other than lysine (SEQ ID NO:3). It is preferred to alter amino acid #396 to an amino acid chosen from the group of isoleucine (SEQ ID NO:4), arginine (SEQ ID NO:5), glutamine (SEQ ID NO:6), histidine (SEQ ID NO:7) or glycine (SEQ ID NO:8). In a particularly preferred embodiment of the present invention amino acid #396 is altered to arginine.

DETAILED DESCRIPTION OF THE INVENTION

As already mentioned, the modified hGAD65 protein having considerably reduced enzymatic activity constitutes an object of the present invention. This altered protein can be used for treating auto-immune diseases, such as IDDM.

"Modified hGAD65 protein" as utilized herein refers to human glutamic acid decarboxylase having a molecular weight of 65 kDa wherein amino acid #396 has been altered to an amino acid other than lysine, and whose enzymatic activity has been considerably reduced. In a preferred embodiment, the altered amino acid is chosen from the group of isoleucine, arginine, glutamine, histidine and glycine. Of these, arginine is considered to be most preferred as it is unable to form a Schiff base, but has similar hydrophobicity (index of both is 3.0) and size compared to lysine. The amino acid sequence of this modified hGAD65 protein is disclosed as SEQ ID NO:5.

The present invention also relates to nucleic acid sequences encoding a modified hGAD65 protein taken into account the degenerated genetic code. A preferred embodiment is disclosed as SEQ ID NO:2.

In an other aspect, the present invention relates to an oligonucleotide that can be used for altering amino acid #396 to an amino acid other than lysine by site-directed mutagenesis of a nucleic acid encoding wild-type hGAD65. A preferred embodiment of such an oligonucleotide is disclosed as SEQ ID NO:1.

In another aspect, the present invention relates to vectors and host cells comprising the above mentioned nucleic acids encoding modified hGAD65 protein. The nucleic acids may be readily introduced into a wide variety of host cells. Representative examples of such host cells include plant cells, eukaryotic cells and prokaryotic cells. Within preferred embodiments, the nucleic acid molecules are introduced into cells from an insect or a vertebrate or warm-blooded anomal, such as a human, macaque, dog, cow, horse, pig, sheep, rat hamster, mouse, or a fish, or any hybrid thereof.

The nucleic acid molecules (or vectors) may be introduced into host cells by a wide variety of mechanisms, including for example calcium phosphate-mediated transfection (Wigler et al., Cell 14:725, 1978, fully incorporated in the description by reference), lipofection; gene gun (Corsaro and Pearson, Somatic Cell Gen. 1:603, 1981; Graham and Van der Eb, Virology 52:456, 1973; both of which are fully incorporated in the description by reference), electroporation (Neumann et al., EMBO J. 1:841–845, 1982, fully incorporated in the description by reference), retroviral, adenoviral protoplast-mediated transfection or DEAE-dextran mediated transfection (Ausubel et al., (eds), Current Protocols in Molecular Biology, John Wiley and Sons, Inc., NY, N.Y., USA 1987, fully incorporated in the description by reference) as well as baculovirus transfection, such as the method described in EP 0 327 180 (fully incorporated in the description by reference).

As noted above, the present invention also provides a variety of pharmaceutical compositions for treating and/or preventing autoimmune diseases, such as IDDM, comprising pharmaceutically active amount of a modified hGAD65 protein along with a pharmaceutically or physiologically acceptible carrier, excipients or diluents. Generally, such carriers should be non-toxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are exemplary appropriate diluents.

In addition, the pharmaceutical compositions of the present invention may be prepared for administration by a variety of routes, including for example orally, sublingually, rectally, intraarticularly, intracranially, intradermally, intramuscularly, intraocularly, intraperitoneally, intravenously or subcutaneously. The compositions can occur as tablets, sublingual tablets, granules, pills, capsules, dragées, solutions, syrups, mixtures, emulsions, suppositorys, aerosols, etc.

Furthermore, the above mentioned nucleic acid molecules can be used as pharmaceuticals and directly be injected into a human or animal in need of such treatment by using a gene gun (Corsaro and Pearson, Somatic Cell Gen. 1:603, 1981; Graham and Van der Eb, Virology 52:456, 1973; both of which are fully incorporated in the description by reference). The treated human or animal body are then able to synthesize the modified hGAD65 according to the present invention.

As already mentioned, GAD is expressed by CNS, but also by islet cells in pancrease even producing insulin. GAD 65 is regarded to be the antigen initiating the immune response leading to diabetes, type 1 (IDDM). A GAD similar antigen has also been identified on Epstein Barr transformed lymphocytes and in coxsaclievirus-infected cells. The influence of GAD 65 and the relation between IDDM and the presence of GAD 65 are described in Kaufman et al., Nature 361:69, 1993; and Nov. 4th, 1993, pp 69–71, incorporated by reference.

Accordingly the present invention concerns a method to prevent and to treat IDDM by inducing a tolerance to GAD as well as a GAD for such a treatment. The method can be used on all or certain population segments with the object to eliminate or to minimize the IDDM frequency, at least of GAD initiated IDDM. The method can be adapted above all to individuals with a genetic predisposition for IDDM and to individuals with an increased antibody titer against GAD with the object to lead the at least in the last mentioned case already started autoimmune reaction in regress. The method can also be used with patients with a developed IDDM to eliminate the possibility of a renewned autoimmune attack after e.g. a pancreas or an islet cell transplantation. The method relates tro modifying the DNA sequence coding GAD in such a way that the efficiency of the produced peptide in the connection with GABA decreases or vanishes without thereby its diabetes autoimmune antigenic features disappearing. In this way GAD can be used more safely for human beings and thus GAD can be administered in various ways for introducing tolerance.

For the participation of GAD as an enzyme during the splitting of Glutamatic Acid into GABA and carbon dioxide the presence of a cofactor PLP (pyridoxal-5'-phosphate) is required. The PLP binding site consists of aminoacid 395–397 of wild type hGAD65. By replacing the aminoacid #396 with another amino acid the binding site for PLP is influenced so that said cofactor PLP is not bound to said binding site on the GAD molecule resulting in that said GAD molecule no longer participates in the GABA synthesis. The modification at said binding site is not influencing the GAD epitope being diabetogenerating. The modified GAD molecule is expressed with a known recombinant technique.

The manufacturing of cDNA from mRNA is well known today. The modified hGAD65 protein produced is then used to treat IDDM.

This modified hGAD65 so obtained is useful as an immunomodulant therapeutic to prevent certain autoimmune diseases (including insulin-dependent diabetes mellitus) and certain other diseases (including neurological diseases). The provision of this is a novel means to avoid (or minimise) the risk of toxicity (e.g. neurotoxicity) possibly arising from the enzyme activity of a GAD-based immunotherapeutic.

From now on, the invention will be described with reference to the enclosed examples. However, it should be understood that the scope of the present invention is not to be restricted to those examples.

Materials and methods

1. DNA oligomer design and synthesis

Both oligos (below) represent sequences from the coding strand of both the insert or vector, and are intended to hybridise to the same (ie. non-coding) strand of p65 (Synectics proprietary clone derived from the cDNA sequence for human GAD65 published by Karlsen et al 1991 Proc. Natl. Acad. Sci USA 88:8337–8341 and Bu et al. 1992 Proc. Natl. Acad. Sci USA 89:2115–2119; both of which are fully incorporated in the description by reference).

The mutagenic primer (SEQ ID NO:1) was designed according to Stratagene recommendations and contained the CGC codon for Arginine, flanked at either end by 14 nts derived from the corresponding hGAD65 cDNA sequence. Of the 6 alternative codons for Arginine (viz. AGA, AGG, CGA, CGC, CGG, CGU), the codon CGC was selected as this has the greatest usage in animals (Grantham R, Gautier C, Gouy M, Jacobzone M, Mercier R 1981 Nucleic Acid Res 9:43–74: fully incorporated in the description by reference). Accordingly, the 31-mer mutagenic oligo has sequence:

5'-CG TGG AAT CCA CAC CGC ATG ATG GGA GTC CC-3' (SEQ ID NO:1)
-corresponding to nt #1186 (upstream end) and #1216 (downstream) of p65. This mutagenic primer (coded "SDM-PLP") was synthesised at the Karonlinska Institute facility, and kinased (via T4 polynycleotide kinase, see Current Protocols in Molecular Biology, John Wiley & Sons, Inc., fully incorporated in the description by reference) prior to use. The Tm of SDM-PLP is estimated as 60° C. and was used during mutagenesis.

The Sca I to Mlu I selection primer was chosen because of the absence of sites in the rhGAD65 insert and the single site in the pGEM4z vector of p65. This kinased primer was supplied by Stratagene (catalogue #300331).

2. Site-directed mutagenesis of proprietary hGAD65 clone "p65"

The Chameleon™ double-stranded DNA site-directed mutagenesis kit from Stratagene was used for modification of the Synectics Biotechnology rhGAD65 clone (coded "p65"), and followed the manufacturers' instructions in the instruction manual (Catalog #200509, Jun. 13, 1994, fully incorporated in the description by reference).

3. DNA sequencing of candidate clones

The required mutation (present in clone #18) was confirmed by DNA sequencing using "Taq DyeDeoxy Terminator Cycle Sequencing" (Applied BioSystems) and "ALF" sequenator at the Karonlinska facility. The sequencing oligo "JR11" (annealing to nts #1353–1369 in the coding strand) was used to confirm sequence at nts "1200–1202. Oligo "JR4" (annealing to the noncoding strand upstream of nts "1200–1202, at nts #1033–1050) was used to obtain seqence in a downstream direction to the site of the mutation.

Methods used for these manipulations followed previously-published procedures (e.g. Current Protocols in Molecular Biology, John Wiley & Sons, Inc; Sambrook, Fritsch & Maniatis Molecular Cloning: A Laboratory Manual. Cold Spring Harbor Laboratory Press, 1989; both of which are fully incorporated in the description by reference).

4. Check for comparable immunoreactivity between mutant and wild-type

Immunoreactivity of the in vitro transcribed/translated mutant rhGAD65 cDNA (clone #18) was shown to be indistinguishable from the original (non-mutant) p65 clone by using IDDM sera in a radioimmunoassay specific for GAD65 autoantibodies (Falorni et al. 1993 Diabetologia 36 (suppl. 1) A45; Falorni et al. 1994 Autoimmunity 19:113–125; both of which are fully incorporated in the description by reference).

This analysis compared immunoreactivity of the mutant and wild-type clones by comparing radioactivity precipitated by ca. 20GAD65-positive IDDM sera on incubation with $^{35}$S-labelled rhGAD65 protein synthesised in vitro from either the wild-type or mutant rhGAD65 cDNA clones.

EXAMPLE 1

Site-directed Mutagenesis of Wild-type hGAD65

An oligonucleotide having the sequence:
5'-CG TGG AAT CCA CAC CGC ATG ATG GGA GTC CC-3' (SEQ ID NO:1)
was synthesized, phosphorylated and used to mutate a cDNA having the sequence of FIG. 2 in Karlsen et al., P.N.A.S. 88:8337, 1991 (incorporated into the description by reference) according the instructions in the above mentioned Chamelon™ kit. Competent *Escherichia coli* F11 rec A cells were transformed with p65 mutant plasmids. Positive clones were screened by DNA sequencing using the Taq DyeDeoxy™ Terminator Cycle Sequencing Kit from Applied Biosystems. A clone containing the desired mutatant were found.

EXAMPLE 2

In Vitro Translation of $^{35}$S-mutant hGAD65

Recombinant modified human GAD65 was produced by in vitro transcription/translation of the cDNA inserted into the pGEM4z vector. The translation reaction was carried out using SP6 RNA polymerase and rabbit reticulocyte lysate. The materials used in the experiment were part of the TNT coupled transcription/translation system from Promega.

The following reaction mixture was prepared:

Plasmid DNA encoding modified hGAD65 (2 mg/ml) 1 $\mu$l

RNAsin (Promega) 1 $\mu$l

TNT buffer 2 $\mu$l

Amino acid mixture (without methionine)(Promega) 1 $\mu$l $^{35}$S-methionine (NEN-Dupont) 4 $\mu$l SP6 RNA polymerase (Promega) 1 $\mu$l Rabbit Reticulocyte lysate (Promega) 25 $\mu$l Water up to 50 $\mu$l The reactions were incubated for 90 minutes at 30° C. At the end of the incubation time, 2 ml from the reaction tube was incubated for 10 minutes at 37° C. with 1M NaOH/2% $H_2O_2$ and 30 minutes on ice with 0.9 ml 25% trichloroacetic acid (TCA) in order to precipitate proteins that may have been formed. The TCA precipitate was collected on a GF-A Whatman glass fibre filter and its radioactivity was evaluated in a liquid scintillation analyser. It was shown that the precipitate was radioactive and hence, modified hGAD65 was formed.

EXAMPLE 3

Immunoprecipitation of 35S-modified hGAD65 with IDDM Sera

In vitro translated modified hGAD65 from example 2 was immunoprecipitated with IDDM sera to test the immunoreactivity. For each serum sample 15000 cpm TCA-precipitable GAD65 was precipitated with 2 $\mu$l of human serum from healthy or diabetic individuals (final serum dilution 1:50). After overnight immunoprecipitation in cold room, antibody bound $^{35}$S-modified hGAD65 was separated from free $^{35}$S-modified hGAD65 by protein A Sepharose using a Multiscreen Assay Millipore system. Immunoprecipitated radioactivity was evaluated in a liquid scintillation analyzer.

Immunoprecipitation of $^{35}$S-modified hGAD65 for diabetic sera was significantly higher than that obtained with sera from healthy persons. The used diabetic sera were previously found positive for antibodies against wild type hGAD65. Hence, it was concluded that modified hGAD65 has an immunoreactivity similar to that of wild type hGAD65.

What is claimed is:

1. A modified glutamic acid decarboxylase comprising amino acid sequence (SEQ ID NO:3):

```
Met Ala Ser Pro Gly Ser Gly Phe Trp Ser Phe Gly Ser
 1               5                  10

Glu Asp Gly Ser Gly Asp Ser Glu Asn Pro Gly Thr Ala
    15                  20                  25

Arg Ala Trp Cys Gln Val Ala Gln Lys Phe Thr Gly Gly
                30                  35

Ile Gly Asn Lys Leu Cys Ala Leu Leu Tyr Gly Asp Ala
40                  45                  50

Glu Lys Pro Ala Glu Ser Gly Gly Ser Gln Pro Pro Arg
    55                  60                  65

Ala Ala Ala Arg Lys Ala Ala Cys Ala Cys Asp Gln Lys
                70                  75

Pro Cys Ser Cys Ser Lys Val Asp Val Asn Tyr Ala Phe
80                  85                  90

Leu His Ala Thr Asp Leu Leu Pro Ala Cys Asp Gly Glu
                95                  100

Arg Pro Thr Leu Ala Phe Leu Gln Asp Val Met Asn Ile
105                 110                 115

Leu Leu Gln Tyr Val Val Lys Ser Phe Asp Arg Ser Thr
        120                 125                 130

Lys Val Ile Asp Phe His Tyr Pro Asn Glu Leu Leu Gln
                135                 140

Glu Tyr Asn Trp Glu Leu Ala Asp Gln Pro Gln Asn Leu
145                 150                 155

Glu Glu Ile Leu Met His Cys Gln Thr Thr Leu Lys Tyr
                160                 165

Ala Ile Lys Thr Gly His Pro Arg Tyr Phe Asn Gln Leu
170                 175                 180

Ser Thr Gly Leu Asp Met Val Gly Leu Ala Ala Asp Trp
        185                 190                 195

Leu Thr Ser Thr Ala Asn Thr Asn Met Phe Thr Tyr Glu
                200                 205

Ile Ala Pro Val Phe Val Leu Leu Glu Tyr Val Thr Leu
210                 215                 220

Lys Lys Met Arg Glu Ile Ile Gly Trp Pro Gly Gly Ser
                225                 230

Gly Asp Gly Ile Phe Ser Pro Gly Gly Ala Ile Ser Asn
235                 240                 245

Met Tyr Ala Met Met Ile Ala Arg Phe Lys Met Phe Pro
                250                 255                 260

Glu Val Lys Glu Lys Gly Met Ala Ala Leu Pro Arg Leu
                265                 270

Ile Ala Phe Thr Ser Glu His Ser His Phe Ser Leu Lys
275                 280                 285

Lys Gly Ala Ala Ala Leu Gly Ile Gly Thr Asp Ser Val
                290                 295

Ile Leu Ile Lys Cys Asp Glu Arg Gly Lys Met Ile Pro
```

```
300                     305                          310
Ser Asp Leu Glu Arg Arg Ile Leu Glu Ala Lys Gln Lys
        315                 320                  325
Gly Phe Val Pro Phe Leu Val Ser Ala Thr Ala Gly Thr
            330                     335
Thr Val Tyr Gly Ala Phe Asp Pro Leu Leu Ala Val Ala
    340                 345                 350
Asp Ile Cys Lys Lys Tyr Lys Ile Trp Met His Val Asp
            355                 360
Ala Ala Trp Gly Gly Gly Leu Leu Met Ser Arg Lys His
365                 370                 375
Lys Trp Lys Leu Ser Gly Val Glu Arg Ala Asn Ser Val
        380                 385                 390
Thr Trp Asn Pro His Xaa Met Met Gly Val Pro Leu Gln
                395                 400
Cys Ser Ala Leu Leu Val Arg Glu Glu Gly Leu Met Gln
405                 410                 415
Asn Cys Asn Gln Met His Ala Ser Tyr Leu Phe Gln Gln
            420                 425
Asp Lys His Tyr Asp Leu Ser Tyr Asp Thr Gly Asp Lys
430                 435                 440
Ala Leu Gln Cys Gly Arg His Val Asp Val Phe Lys Leu
        445                 450                 455
Trp Leu Met Trp Arg Ala Lys Gly Thr Thr Gly Phe Glu
                460                 465
Ala His Val Asp Lys Cys Leu Glu Leu Ala Glu Tyr Leu
    470                 475                 480
Tyr Asn Ilr Ile Lys Asn Arg Glu Gly Tyr Glu Met Val
            485                 490
Phe Asp Gly Lys Pro Gln His Thr Asn Val Cys Phe Trp
495                 500                 505
Tyr Ile Pro Pro Ser Leu Arg Thr Leu Glu Asp Asn Glu
        510                 515                 520
Glu Arg Met Ser Arg Leu Ser Lys Val Ala Pro Val Ile
                525                 530
Lys Ala Arg Met Met Glu Tyr Gly Thr Thr Met Val Ser
535                 540                 545

Tyr Gln Pro Leu Gly Asp Lys Val Asn Phe Phe Arg Met
                550                     555
Val Ile Ser Asn Pro Ala Ala Thr His Gln Asp Ile Asp
560                 565                 570
Phe Leu Ile Glu Glu Ile Glu Arg Leu Gly Gln Asp Leu
        575                 580                 585
``` wherein Xaa represents a L amino acid chosen from the group of isoleucine (SEQ ID NO:4), arginine (SEQ ID NO:5), glutamine (SEQ ID NO:6), histidine (SEQ ID NO:7) and glycine (SEQ ID NO:8).

2. A modified glutamic acid decarboxylase according to claim 1, wherein Xaa is arginine (SEQ ID NO:5).

3. A nucleotide sequence encoding a modified glutamic acid decarboxylase according to claim 1.

4. A nucleotide sequence according to claim 3 which is the one disclosed herein as SEQ ID NO:2.

5. A vector containing the nucleic acid sequence according to claim 3.

6. A host cell containing a vector according to claim 5.

7. A procedure for producing a modified glutamic acid decarboxylase comprising cultivating a host cell according to claim 6.

8. A pharmaceutical composition comprising a therapeutically effective amount of a modified glutamic acid decarboxylase according to claim 1 together with a pharmaceutically acceptable excipient.

9. A method for treating and/or preventing autoimmune disorders, comprising administering to a human or animal in need thereof, an effective amount of a modified glutamic acid decarboxylase according to claim 1, said amount being effective to treat and/or prevent said autoimmune disorder.

10. An oligonucleotide encoding a modified portion of a modified glutamic acid decarboxylase, wherein said modified portion encodes the amino acid sequence consisting of amino acids 391–400 of SEQ ID NO:3, wherein the amino acid at postion 396 of SEQ ID NO:3 is replaced with an amino acid selected from the group consisting of isoleucine (SEQ ID NO:11), arginine (SEQ ID NO:10), glutamine (SEQ ID NO:12), histidine (SEQ ID NO:13) and glycine (SEQ ID NO:14).

11. An oligonucleotide according to claim 10 comprising the sequence disclosed as SEQ ID NO:1.

* * * * *

SEQUENCE LISTING

<160> NUMBER OF SEQ ID NOS: 14

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide for altering residue No. 396 of hGAD65

<400> SEQUENCE: 1
cgtggaatcc acaccgcatg atgggagtcc c                            31

<210> SEQ ID NO 2
<211> LENGTH: 1761
<212> TYPE: DNA
<213> ORGANISM: Artificial Sequence
<220> FEATURE:
<223> OTHER INFORMATION: Description of Artificial Sequence:Artificial
      gene encoding mutant hGAD65

<400> SEQUENCE: 2
atggcatctc cgggctctgg cttttggtct ttcgggtcgg aagatggctc tggggattcc      60
gagaatcccg gcacagcgcg agcctggtgc caagtggctc agaagttcac gggcggcatc     120
ggaaacaaac tgtgcgccct gctctacgga gacgccgaga gccggcgga gagcggcggg      180 agccaacccc cgcgggccgc cgcccggaag gccgcctgcg cctgcgacca gaagccctgc     240
agctgctcca agtggatgt caactacgcg tttctccatg caacagacct gctgccggcg      300
tgtgatggag aaaggcccac tttggcgttt ctgcaagatg ttatgaacat tttacttcag     360
tatgtggtga aagtttcga tagatcaacc aaagtgattg atttccatta tcctaatgag      420
cttctccaag aatataattg ggaattggca gaccaaccac aaaatttgga ggaaattttg     480
atgcattgcc aaacaactct aaaatatgca attaaaacag gcatcctag atacttcaat      540 caactttcta ctggtttgga tatggttgga ttagcagcag actggctgac atcaacagca     600
aatactaaca tgttcaccta tgaaattgct ccagtatttg tgcttttgga atatgtcaca     660
ctaaagaaaa tgagagaaat cattggctgg ccagggggct ctggccatgg gatattttct     720
cccggtggcg ccatatctaa catgtatgcc atgatgatcg cagcgtttaa gatgttccca     780
gaagtcaagg agaaaggaat ggctgctctt cccaggctca ttgccttcac gtctgaacat     840
agtcattttt ctctcaagaa gggagctgca gccgtaggga ttggaacaga cagcgtgatt     900
ctgattaaat gtgatgagag agggaaaatg attccatctg atcttgaaag aaggattctt     960
gaagccaaac agaaagggtt tgttccttc ctcgtgagtg ccacagctgg aaccaccgtg     1020
tacggagcat tgaccccct cttagctgtc gctgacattt gcaaaagta taagatctgg     1080 atgcatgtgg atgcagcttg gggtgggga ttactgatgt cccgaaaaca caagtggaaa      1140
ctgagtggcg tggagagggc caactctgtg acgtggaatc cacaccgcat gatgggagtc     1200
cctttgcagt gctctgctct cctggttaga gaagagggat tgatgcagaa ttgcaaccaa     1260
atgcatgcct cctacctctt tcagcaagat aaacattatg acctgtccta tgacactgga     1320
gacaaggcct acagtgcgg acgccacgtt gatgttttta actatggct gatgtggagg     1380 gcaaagggga ctaccgggtt tgaagcgcat gttgataaat gtttggagtt ggcagagtat     1440
ttatacaaca tcataaaaaa ccgagaagga tatgagatgg tgtttgatgg aagcctcag     1500 cacacaaatg tctgcttctg gtacattcct ccaagcttgc gtactctgga agacaatgaa     1560

```
gagagaatga gtcgcctctc gaaggtggct ccagtgatta aagccagaat gatggagtat   1620
ggaaccacaa tggtcagcta ccaaccttg  ggagacaagg tcaatttctt ccgcatggtc   1680
atctcaaacc cagcggcaac tcaccaagac attgacttcc tgattgaaga aatagaacgc   1740
cttggacaag atttataata a                                             1761
```

<210> SEQ ID NO 3
<211> LENGTH: 585
<212> TYPE: PRT
<213> ORGANISM: Artificial Sequence
<220> FEATURE:
<223> OTHER INFORMATION: Description of Artificial Sequence:Modified,
      non-enzymically active hGAD65 retaining the
      immunoreactive characteristics of wild type hGAD65.
      Xaa at position 396 is Ile, Arg, Gln, His or Gly.

<400> SEQUENCE: 3

```
Met Ala Ser Pro Gly Ser Gly Phe Trp Ser Phe Gly Ser Glu Asp Gly
  1               5                  10                  15

Ser Gly Asp Ser Glu Asn Pro Gly Thr Ala Arg Ala Trp Cys Gln Val
             20                  25                  30

Ala Gln Lys Phe Thr Gly Gly Ile Gly Asn Lys Leu Cys Ala Leu Leu
         35                  40                  45

Tyr Gly Asp Ala Glu Lys Pro Ala Glu Ser Gly Gly Ser Gln Pro Pro
     50                  55                  60

Arg Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                 85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300
```

-continued

```
Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
                355                 360                 365

Gly Gly Leu Leu Met Ser Arg Lys His Lys Trp Lys Leu Ser Gly Val
        370                 375                 380

Glu Arg Ala Asn Ser Val Thr Trp Asn Pro His Xaa Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
                435                 440                 445

His Val Asp Val Phe Lys Leu Trp Leu Met Trp Arg Ala Lys Gly Thr
450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
                500                 505                 510

Leu Arg Thr Leu Glu Asp Asn Glu Glu Arg Met Ser Arg Leu Ser Lys
                515                 520                 525

Val Ala Pro Val Ile Lys Ala Arg Met Met Glu Tyr Gly Thr Thr Met
                530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
                580                 585

<210> SEQ ID NO 4
<211> LENGTH: 585
<212> TYPE: PRT
<213> ORGANISM: Artificial Sequence
<220> FEATURE:
<223> OTHER INFORMATION: Description of Artificial Sequence:Modified
      hGAD

<400> SEQUENCE: 4

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
        50                  55                  60

Arg Ala Ala Ala Arg Lys Ala Ala Cys Ala Cys Asp Gln Lys Pro Cys
65              70                  75                  80
```

-continued

```
Ser Cys Ser Lys Val Asp Val Asn Tyr Ala Phe Leu His Ala Thr Asp
                 85                  90                  95

Leu Leu Pro Ala Cys Asp Gly Glu Arg Pro Thr Leu Ala Phe Leu Gln
            100                 105                 110

Asp Val Met Asn Ile Leu Gln Tyr Val Val Lys Ser Phe Asp Arg
        115                 120                 125

Ser Thr Lys Val Ile Asp Phe His Tyr Pro Asn Glu Leu Leu Gln Glu
        130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
                180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
        210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
        290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
        370                 375                 380

Glu Arg Ala Asn Ser Val Thr Trp Asn Pro His Ile Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
        450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495
```

```
Gly Lys Pro Gln His Thr Asn Val Cys Phe Trp Tyr Ile Pro Pro Ser
            500                 505                 510

Leu Arg Thr Leu Glu Asp Asn Glu Arg Met Ser Arg Leu Ser Lys
            515                 520                 525

Val Ala Pro Val Ile Lys Ala Arg Met Met Glu Tyr Gly Thr Thr Met
            530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 5
<211> LENGTH: 585
<212> TYPE: PRT
<213> ORGANISM: Artificial Sequence
<220> FEATURE:
<223> OTHER INFORMATION: Description of Artificial Sequence:Modified
      hGAD

<400> SEQUENCE: 5

Met Ala Ser Pro Gly Ser Gly Phe Trp Ser Phe Gly Ser Glu Asp Gly
  1               5                  10                  15

Ser Gly Asp Ser Glu Asn Pro Gly Thr Ala Arg Ala Trp Cys Gln Val
                 20                  25                  30

Ala Gln Lys Phe Thr Gly Gly Ile Gly Asn Lys Leu Cys Ala Leu Leu
             35                  40                  45

Tyr Gly Asp Ala Glu Lys Pro Ala Glu Ser Gly Gly Ser Gln Pro Pro
 50                  55                  60

Arg Ala Ala Ala Arg Lys Ala Ala Cys Ala Cys Asp Gln Lys Pro Cys
 65                  70                  75                  80

Ser Cys Ser Lys Val Asp Val Asn Tyr Ala Phe Leu His Ala Thr Asp
                 85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
            115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
            195                 200                 205

Ile Ala Pro Val Phe Val Leu Leu Glu Tyr Val Thr Leu Lys Lys Met
            210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270
```

```
Leu Ile Ala Phe Thr Ser Glu His Ser His Phe Ser Leu Lys Lys Gly
            275                 280                 285

Ala Ala Ala Leu Gly Ile Gly Thr Asp Ser Val Ile Leu Ile Lys Cys
            290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
            370                 375                 380

Glu Arg Ala Asn Ser Val Thr Trp Asn Pro His Arg Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
            435                 440                 445

His Val Asp Val Phe Lys Leu Trp Leu Met Trp Arg Ala Lys Gly Thr
            450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
            530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 6
<211> LENGTH: 585
<212> TYPE: PRT
<213> ORGANISM: Artificial Sequence
<220> FEATURE:
<223> OTHER INFORMATION: Description of Artificial Sequence:Modified
      hGAD

<400> SEQUENCE: 6

Met Ala Ser Pro Gly Ser Gly Phe Trp Ser Phe Gly Ser Glu Asp Gly
  1               5                  10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
```

-continued

```
                35                  40                  45
        Tyr Gly Asp Ala Glu Lys Pro Ala Glu Ser Gly Ser Gln Pro Pro
                50                  55                  60
        Arg Ala Ala Arg Lys Ala Ala Cys Ala Cys Asp Gln Lys Pro Cys
        65                  70                  75                  80
        Ser Cys Ser Lys Val Asp Val Asn Tyr Ala Phe Leu His Ala Thr Asp
                        85                  90                  95
        Leu Leu Pro Ala Cys Asp Gly Glu Arg Pro Thr Leu Ala Phe Leu Gln
                        100                 105                 110
        Asp Val Met Asn Ile Leu Leu Gln Tyr Val Val Lys Ser Phe Asp Arg
                    115                 120                 125
        Ser Thr Lys Val Ile Asp Phe His Tyr Pro Asn Glu Leu Leu Gln Glu
                    130                 135                 140
        Tyr Asn Trp Glu Leu Ala Asp Gln Pro Gln Asn Leu Glu Glu Ile Leu
        145                 150                 155                 160
        Met His Cys Gln Thr Thr Leu Lys Tyr Ala Ile Lys Thr Gly His Pro
                        165                 170                 175
        Arg Tyr Phe Asn Gln Leu Ser Thr Gly Leu Asp Met Val Gly Leu Ala
                        180                 185                 190
        Ala Asp Trp Leu Thr Ser Thr Ala Asn Thr Asn Met Phe Thr Tyr Glu
                    195                 200                 205
        Ile Ala Pro Val Phe Val Leu Leu Glu Tyr Val Thr Leu Lys Lys Met
                210                 215                 220
        Arg Glu Ile Ile Gly Trp Pro Gly Gly Ser Gly Asp Gly Ile Phe Ser
        225                 230                 235                 240
        Pro Gly Gly Ala Ile Ser Asn Met Tyr Ala Met Met Ile Ala Arg Phe
                        245                 250                 255
        Lys Met Phe Pro Glu Val Lys Glu Lys Gly Met Ala Ala Leu Pro Arg
                        260                 265                 270
        Leu Ile Ala Phe Thr Ser Glu His Ser His Phe Ser Leu Lys Lys Gly
                    275                 280                 285
        Ala Ala Ala Leu Gly Ile Gly Thr Asp Ser Val Ile Leu Ile Lys Cys
                    290                 295                 300
        Asp Glu Arg Gly Lys Met Ile Pro Ser Asp Leu Glu Arg Arg Ile Leu
        305                 310                 315                 320
        Glu Ala Lys Gln Lys Gly Phe Val Pro Phe Leu Val Ser Ala Thr Ala
                        325                 330                 335
        Gly Thr Thr Val Tyr Gly Ala Phe Asp Pro Leu Leu Ala Val Ala Asp
                        340                 345                 350
        Ile Cys Lys Lys Tyr Lys Ile Trp Met His Val Asp Ala Ala Trp Gly
                    355                 360                 365
        Gly Gly Leu Leu Met Ser Arg Lys His Lys Trp Lys Leu Ser Gly Val
                370                 375                 380
        Glu Arg Ala Asn Ser Val Thr Trp Asn Pro His Gln Met Met Gly Val
        385                 390                 395                 400
        Pro Leu Gln Cys Ser Ala Leu Leu Val Arg Glu Glu Gly Leu Met Gln
                        405                 410                 415
        Asn Cys Asn Gln Met His Ala Ser Tyr Leu Phe Gln Gln Asp Lys His
                        420                 425                 430
        Tyr Asp Leu Ser Tyr Asp Thr Gly Asp Lys Ala Leu Gln Cys Gly Arg
                    435                 440                 445
        His Val Asp Val Phe Lys Leu Trp Leu Met Trp Arg Ala Lys Gly Thr
        450                 455                 460
```

```
Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
                580                 585

<210> SEQ ID NO 7
<211> LENGTH: 585
<212> TYPE: PRT
<213> ORGANISM: Artificial Sequence
<220> FEATURE:
<223> OTHER INFORMATION: Description of Artificial Sequence:Modified
      hGAD

<400> SEQUENCE: 7

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
    50                  55                  60

Arg Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
    115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
    195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
```

```
225                 230                 235                 240
Pro Gly Gly Ala Ile Ser Asn Met Tyr Ala Met Met Ile Ala Arg Phe
                245                 250                 255
Lys Met Phe Pro Glu Val Lys Glu Lys Gly Met Ala Ala Leu Pro Arg
                260                 265                 270
Leu Ile Ala Phe Thr Ser Glu His Ser His Phe Ser Leu Lys Lys Gly
                275                 280                 285
Ala Ala Ala Leu Gly Ile Gly Thr Asp Ser Val Ile Leu Ile Lys Cys
                290                 295                 300
Asp Glu Arg Gly Lys Met Ile Pro Ser Asp Leu Glu Arg Arg Ile Leu
305                 310                 315                 320
Glu Ala Lys Gln Lys Gly Phe Val Pro Phe Leu Val Ser Ala Thr Ala
                325                 330                 335
Gly Thr Thr Val Tyr Gly Ala Phe Asp Pro Leu Leu Ala Val Ala Asp
                340                 345                 350
Ile Cys Lys Lys Tyr Lys Ile Trp Met His Val Asp Ala Ala Trp Gly
                355                 360                 365
Gly Gly Leu Leu Met Ser Arg Lys His Lys Trp Lys Leu Ser Gly Val
                370                 375                 380
Glu Arg Ala Asn Ser Val Thr Trp Asn Pro His His Met Met Gly Val
385                 390                 395                 400
Pro Leu Gln Cys Ser Ala Leu Leu Val Arg Glu Glu Gly Leu Met Gln
                405                 410                 415
Asn Cys Asn Gln Met His Ala Ser Tyr Leu Phe Gln Gln Asp Lys His
                420                 425                 430
Tyr Asp Leu Ser Tyr Asp Thr Gly Asp Lys Ala Leu Gln Cys Gly Arg
                435                 440                 445
His Val Asp Val Phe Lys Leu Trp Leu Met Trp Arg Ala Lys Gly Thr
                450                 455                 460
Thr Gly Phe Glu Ala His Val Asp Lys Cys Leu Glu Leu Ala Glu Tyr
465                 470                 475                 480
Leu Tyr Asn Ile Ile Lys Asn Arg Glu Gly Tyr Glu Met Val Phe Asp
                485                 490                 495
Gly Lys Pro Gln His Thr Asn Val Cys Phe Trp Tyr Ile Pro Pro Ser
                500                 505                 510
Leu Arg Thr Leu Glu Asp Asn Glu Glu Arg Met Ser Arg Leu Ser Lys
                515                 520                 525
Val Ala Pro Val Ile Lys Ala Arg Met Met Glu Tyr Gly Thr Thr Met
                530                 535                 540
Val Ser Tyr Gln Pro Leu Gly Asp Lys Val Asn Phe Phe Arg Met Val
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
                580                 585

<210> SEQ ID NO 8
<211> LENGTH: 585
<212> TYPE: PRT
<213> ORGANISM: Artificial Sequence
<220> FEATURE:
<223> OTHER INFORMATION: Description of Artificial Sequence:Modified
      hGAD

<400> SEQUENCE: 8
```

-continued

```
Met Ala Ser Pro Gly Ser Gly Phe Trp Ser Phe Gly Ser Glu Asp Gly
 1               5                  10                 15

Ser Gly Asp Ser Glu Asn Pro Gly Thr Ala Arg Ala Trp Cys Gln Val
             20                  25                 30

Ala Gln Lys Phe Thr Gly Gly Ile Gly Asn Lys Leu Cys Ala Leu Leu
         35                  40                  45

Tyr Gly Asp Ala Glu Lys Pro Ala Glu Ser Gly Ser Gln Pro Pro
     50                  55                  60

Arg Ala Ala Arg Lys Ala Ala Cys Ala Cys Asp Gln Lys Pro Cys
 65              70                  75                  80

Ser Cys Ser Lys Val Asp Val Asn Tyr Ala Phe Leu His Ala Thr Asp
             85                  90                  95

Leu Leu Pro Ala Cys Asp Gly Glu Arg Pro Thr Leu Ala Phe Leu Gln
             100                 105                 110

Asp Val Met Asn Ile Leu Leu Gln Tyr Val Lys Ser Phe Asp Arg
         115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
        180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
            245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Gly Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
```

420                 425                 430
Tyr Asp Leu Ser Tyr Asp Thr Gly Asp Lys Ala Leu Gln Cys Gly Arg
            435                 440                 445
His Val Asp Val Phe Lys Leu Trp Leu Met Trp Arg Ala Lys Gly Thr
        450                 455                 460
Thr Gly Phe Glu Ala His Val Asp Lys Cys Leu Glu Leu Ala Glu Tyr
465                 470                 475                 480
Leu Tyr Asn Ile Ile Lys Asn Arg Glu Gly Tyr Glu Met Val Phe Asp
                485                 490                 495
Gly Lys Pro Gln His Thr Asn Val Cys Phe Trp Tyr Ile Pro Pro Ser
            500                 505                 510
Leu Arg Thr Leu Glu Asp Asn Glu Glu Arg Met Ser Arg Leu Ser Lys
        515                 520                 525
Val Ala Pro Val Ile Lys Ala Arg Met Met Glu Tyr Gly Thr Thr Met
    530                 535                 540
Val Ser Tyr Gln Pro Leu Gly Asp Lys Val Asn Phe Phe Arg Met Val
545                 550                 555                 560
Ile Ser Asn Pro Ala Ala Thr His Gln Asp Ile Asp Phe Leu Ile Glu
                565                 570                 575
Glu Ile Glu Arg Leu Gly Gln Asp Leu
            580                 585

<210> SEQ ID NO 9
<211> LENGTH: 10
<212> TYPE: PRT
<213> ORGANISM: Homo sapiens
<220> FEATURE:
<223> OTHER INFORMATION: Description of Artificial Sequence:PLP binding
      site of hGAD65

<400> SEQUENCE: 9

Thr Trp Asn Pro His Lys Met Met Gly Val
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence:Mutant PLP
      binding site of hGAD65

<400> SEQUENCE: 10

Thr Trp Asn Pro His Arg Met Met Gly Val
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence:Mutant PLP
      binding site of hGAD65

<400> SEQUENCE: 11

Thr Trp Asn Pro His Ile Met Met Gly Val
 1               5                  10

<210> SEQ ID NO 12
<211> LENGTH: 10
<212> TYPE: PRT
<213> ORGANISM: Artificial Sequence

```
<220> FEATURE:
<223> OTHER INFORMATION: Description of Artificial Sequence:Mutant PLP
      binding site of hGAD65

<400> SEQUENCE: 12

Thr Trp Asn Pro His Gln Met Met Gly Val
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:Mutant PLP
      binding site of hGAD65

<400> SEQUENCE: 13

Thr Trp Asn Pro His His Met Met Gly Val
 1               5                  10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence:Mutant PLP
      binding site of hGAD65

<400> SEQUENCE: 14

Thr Trp Asn Pro His Gly Met Met Gly Val
 1               5                  10
```